United States Patent [19]

Attardo et al.

[11] Patent Number: 5,348,946
[45] Date of Patent: Sep. 20, 1994

[54] HETEROANTHRACYCLINE ANTITUMOR ANALOGS

[75] Inventors: Giorgio G. Attardo, St. Leonard; Bernard Belleau, deceased, late of Westmount, both of Canada, by Pierrette Belleau executrix

[73] Assignee: Biochem Immunosystems, Inc., Montreal, Canada

[21] Appl. No.: 751,092

[22] Filed: Aug. 28, 1991

Related U.S. Application Data

[63] Continuation of Ser. No. 661,376, Feb. 28, 1991, abandoned.

[51] Int. Cl.$^5$ .................. A61K 31/70; C07H 15/24
[52] U.S. Cl. ............................... 514/34; 536/6.4; 536/18.1
[58] Field of Search ............ 536/6.9, 10.1, 18.1; 514/34; 544/1, 14, 63, 100, 244; 548/420, 421, 426; 549/13, 14, 15, 20, 24, 29, 72, 200, 356, 357, 429

[56] References Cited

U.S. PATENT DOCUMENTS

| | | | |
|---|---|---|---|
| 4,464,259 | 8/1983 | Mosher et al. | 536/6.4 |
| 4,585,760 | 4/1986 | Lee | 514/34 |
| 4,697,005 | 9/1987 | Swenton et al. | 536/6.4 |
| 4,877,870 | 10/1989 | Umezawa et al. | 536/6.4 |

FOREIGN PATENT DOCUMENTS

| | | | |
|---|---|---|---|
| 0269339 | 6/1988 | European Pat. Off. | 536/6.4 |
| 2225781A | 6/1990 | United Kingdom | |

OTHER PUBLICATIONS

Matsuzawa et al. "Structure–activity relationships..." The Jour. of Antibiotics, vol. 34, No. 12, Dec. 1981, Tokyo, pp. 1596–1607.
Mitscher, L. A. et al. "Total chemical synthesis..." Jour. of Medicinal Chem., vol. 29 (1986), Ame. Chem. Soc. Washington, U.S. pp. 1277–1281.
Tu, Y. "Total synthesis of..." Jour of Organic Chem. vol. 52 No. 25 (1987), Ame. Chem. Soc., Easton, US, pp. 5624–5627.
Beard, A. R. et al. "Synthesis of analogues..." Tetrahedron (incl. Tetrahedron Reports, vol. 43 No. 1987, Oxford, GB, pp. 4207–4215.
Chemical Abstracts #89900y, vol. 84, 1976, Columbus, Ohio, US, p. 503.
Chemical Abstracts #22775p, vol. 85 1976, Columbus, Ohio, US, p. 73.
Boddy, I. K. et al. "Experiments directed towards..." Chemical Abstracts #134161q, vol. 107, 1987, Columbus, Ohio, US, p. 708.
Krohn S. et al. "Synthetic anthracyclines..." Chemical Abstracts #203760d, vol. 90, 1979, Columbus, Ohio US, p. 593.
Charlton, J. L. et al. "Photochemical synthesis..." Tetrahedron Letters, vol. 25, No. 25, 1984, Pergamon Press Ltd., Oxford, GB, pp. 2663–1666.
Durst, T. et al. "Stereoselectivity in the Diels–Alder..." Jour of Organic Chem vol. 50 No. 4, 1985, Ame Chem Soc, Easton, U.S., pp. 4829–4833.
Charlton, J. L. et al. "Diastereoselectivity and asymmetric..." Canadian Jour of Chem, vol. 64 No. 4, Apr. 1986, Ottawa, CA, pp. 720–725.

*Primary Examiner*—Johnnie R. Brown
*Assistant Examiner*—Elli Peselev
*Attorney, Agent, or Firm*—Nixon & Vanderhye

[57] ABSTRACT

Heterocyclic antitumor compounds are described, which are useful in the treatment of cancer and tumors in vitro, such as breast cancer, leukemia, lung cancer, colon cancer, ovarian cancer, renal cancer, CNS cancer and melanoma. Pharmaceutical compositions and method of preparing the compounds are also described.

22 Claims, No Drawings

HETEROANTHRACYCLINE ANTITUMOR ANALOGS

This is a continuation of 07/661,376 filed Feb. 28, 1991, now abandoned.

The present invention relates to a novel class of antitumor derivatives, to processes and to intermediates for preparing the derivatives, to pharmaceutical compositions containing them and to the use of those derivatives as in vitro antitumor agents. More specifically, the present invention relates to ring A and C backbone modified analogs of doxorubicin.

BACKGROUND OF THE INVENTION

Anthracycline antibiotics including doxorubicin and daunorubicin are important chemotherapeutic agents in the treatment of a broad spectrum of neoplastic conditions. While daunorubicin (1) is clinically used mainly against acute childhood and adult leukemias, doxorubicin (2), also known as adriamycin, has the widest spectrum of antitumor activity of all chemotherapeutic agents (Weiss, R. B., Sarosy, G., Clagett-Carr, K., Russo, M. and Leyland-Jones, B., Cancer Chemother. Pharmacol., 18, 185-197, 1986; Arcamone, F., Doxorubicin, Academic Press, New York, 1980).

The usefulness of known anthracycline antibiotics is compromised by dose limiting toxicities such as myelosuppression (Crooke, S. K., Anthracyclines; Current Status and New Developments, Academic Press, New York 1980) and cardiotoxicity (Olson, R. D. et al, Proc. Natl. Acad. Sci., USA 85 3585-3589, 1988 and references therein) as well as the resistance from treated tumors (Mimnaugh, E. G. et al, Cancer Research, 49, 8-15, 1989; McGrath, T. et al, Biochemical Pharmacology, 38 497-501, 1989). In view of the proven effectiveness of known anthracyclines in the treatment of cancer, efforts have been undertaken to develop anthracycline analogs with either an improved therapeutic index or with reduced cross-resistance.

Several thousands of anthracycline derivatives have been obtained either from streptomyces biosynthesis or via the semisynthetic modification of known natural anthracycline antibiotics (Arcamone, F., Doxorubicin, Academic Press, New York 1980; Thomson, R. H., Naturally Occurring Quinones III: Recent Advances, Chapman and Hall, New York 1987; Anthracyclines: Current Status and New Developments, Academic Press, New York, 1980; Brown, J. R. and Iman, S. H., Recent Studies on Doxorubicin and its Analogues, Prog. Med. Chem. 21 170-236, 1984; Brown, J. R. Adriamycin and Related Anthracycline Antibiotics, Prog. Med. Chem., 15, 125-164, 1978). The majority of known anthracyclines show two types of structural differences: (i) the substitution pattern of the aglycone tetracyclic ring system, and (ii) the structure and number of glycosides attached at C-7 or C-10 (doxorubicin numbering). Some examples of the structural diversity of anthracycline antibiotics are shown below.

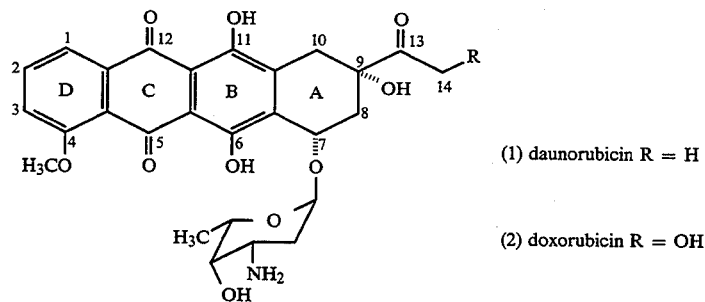

(1) daunorubicin R = H (2) doxorubicin R = OH

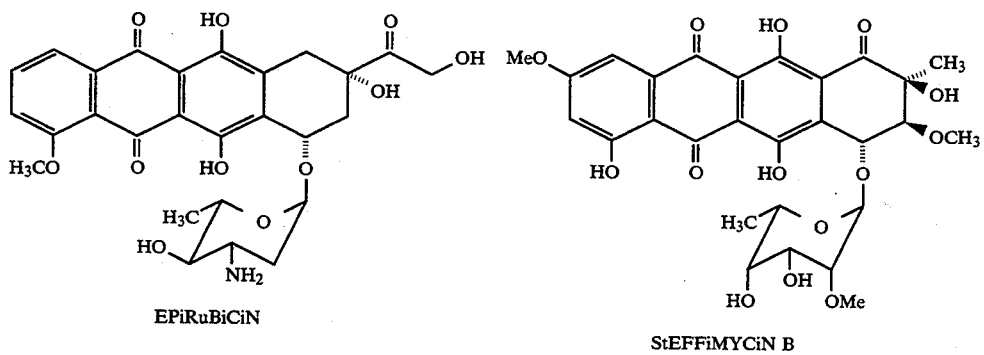

EPiRuBiCiN

StEFFiMYCiN B

-continued

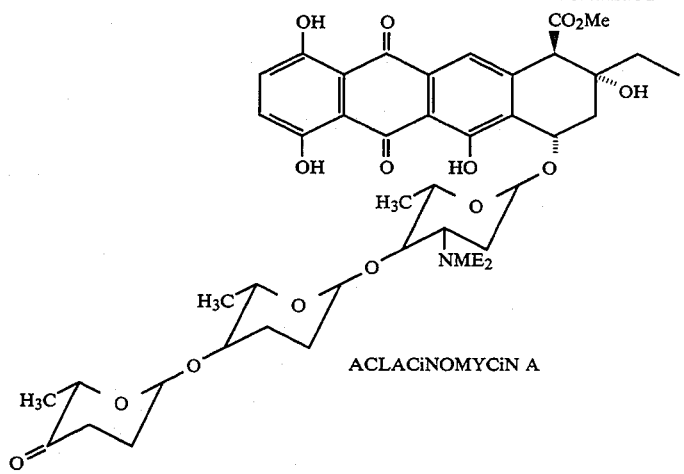

ACLACiNOMYCiN A

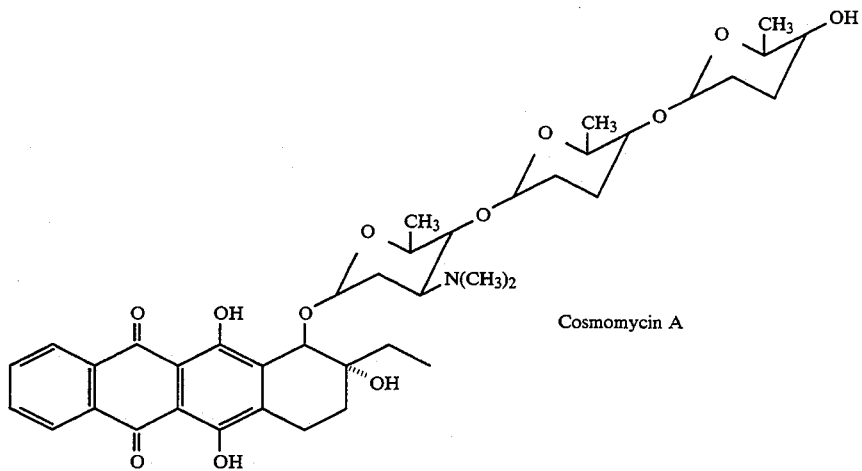

Cosmomycin A

In contrast to the great number of derivatives obtained from these two kinds of structural modifications, there has been little effort towards the synthesis and biological evaluation of ring-A and C heteroanthracycline analogs. Some xantho [2,3-g] tetralines 3, 4, 5 (see below) have been reported to possess antileukemic activity, but lower than that of the parent antibiotics daunorubicin and doxorubicin (J. W. Lown and S. M. Sondhi, J. Org. Chem., 50, 1413 (1985); J. W. Lown et al, Drugs Exp. Clin. Res., 10, 735 (1984). Farmitalia Carlo Erba S.R.L. has investigated ring A modified analogs of daunorubicin and doxorubicin, and has reported 10-noranthracyclines 6 and 7 as exhibiting antitumor activity (see, for example, German Offen. D.E. 3,915,041 (Cl. C07H15/252), Feb. 22, 1990; G.B. Pat. Appln 88/11,413, May 13, 1988). Examples of other antineoplastic agents which possess a heterocyclic central ring but which bear no relation to the anthrcyclines include hycanthone 8 (Remers, W. A., "Antineoplastic Agents", John Wiley & Sons, New York, N.Y. 1984), 1-nitro-9-aminoacridines 9 (Mazerska, Z, et al, Arzneim-Forsch., 40(4), 472 (1990)), and 9-oxoxanthene-4-acetic acids 10 (Atwell, G. J., et al, J. Mad. Chem., 33 (5), 1375 (1990).

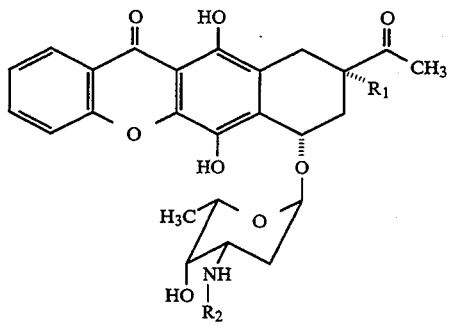

3: $R_1 = R_2 = H$
4: $R_1 = OH, R_2 = H$
5: $R_1 = OH, R_2 = COCF_3$

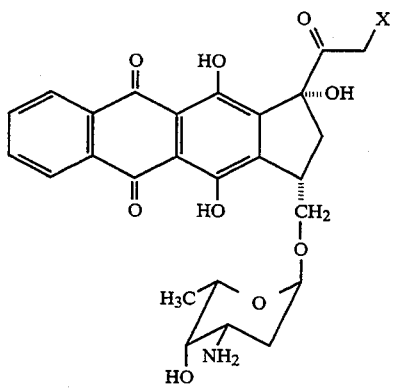

6: $X = H$
7: $X = OH$

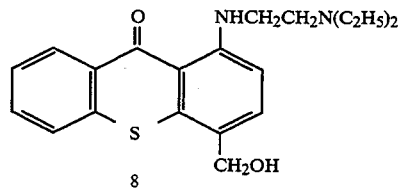

8

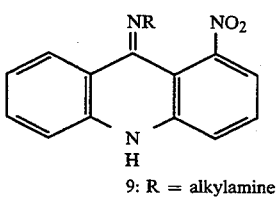

9: R = alkylamine

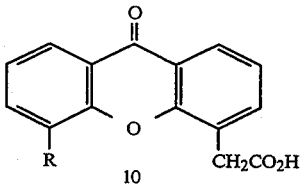

10

DESCRIPTION OF THE INVENTION

The present invention provides novel heterocyclic anthracyclines which are structurally distinguished from the prior art compounds by the nature of the rings A and C of the anthracyclinone moiety. More specifically, the compounds of the present invention are structurally distinguished from prior art compounds by possessing an uncommon tetracyclic moiety with a five-membered A ring and an optional hetero D ring. This structurally distinct class of compounds exhibits therapeutic activity, in particular in vitro anticancer and antitumor activity.

In one aspect of the invention, there is provided a compound of the formula (11):

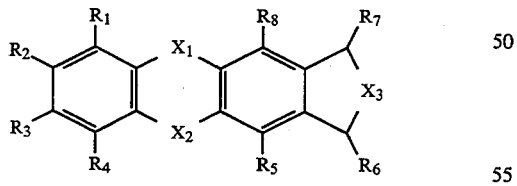

wherein
$X_1$ and $X_2$ are independently selected from the group consisting of
$CH_2$
CHOH
C=O
O
S
SO
$SO_2$
NH
NO
C=N(R), wherein R is selected from the group consisting of
hydrogen
$C_{1-16}$ alkyl
$C_{1-16}$ acyl and
$C_{1-16}$ alkylamine, and
NR, wherein R is selected from the group consisting of
$C_{1-16}$ acyl
$C_{1-16}$ alkyl and
aryl;
$X_3$ is selected from the group consisting of
O
S
C=O
SO
$SO_2$
NH
$CH_2$
$C(R_{13})(R_{14})$, wherein $R_{13}$ and $R_{14}$ are independently selected from the group consisting of
hydrogen
aryl
$C_{1-16}$ alkyl
$C_{1-16}$ alkoxy
$C_{1-16}$ hydroxyalkyl
$C_{3-8}$ cycloalkyl
cyano
hydroxy
arylsulphone
$C_{1-16}$ alkylsulphide
acyl of the formula —C(R)=O, wherein R is selected from the group consisting of
hydrogen
$C_{1-16}$ alkyl
$C_{3-8}$ cycloalkyl, hydroxyalkyl,
alkoxyalkyl,
araloxyalkyl,
acyloxyalkyl,
amino which may be unsubstituted or mono- or di-substituted, and
an naturally occurring amino acid, for example alanine, arginine, cysteine, glycine, leucine, lysine, methionine and the like, or a synthetic amino acid;
a group of the formula —C(OR)=O, wherein R is selected from the group consisting of
hydrogen,
$C_{1-16}$ alkyl,
$C_{3-8}$ cycloalkyl,
hydroxyalkyl,
alkoxyalkyl,
aryloxyalkyl,
araloxyalkyl,
aryl, and
aralkyl;
a group of the formula —CH$_2$C(OR)=O, wherein R is selected from the group consisting of
hydrogen
$C_{1-16}$ alkyl
$C_{3-8}$ cycloalkyl
hydroxyalkyl
alkoxyalkyl
aryloxyalkyl
araloxyalkyl
aryl
aralkyl and
amino which may be unsubstituted or mono- or di-substituted;
$R_1$, $R_2$, $R_3$, $R_4$, $R_5$ and $R_8$ are independently selected from the group consisting of
hydrogen,
hydroxyl,
$C_{1-16}$ alkyl,
$C_{1-16}$ alkoxyl,
$C_{2-16}$ alkenyl,
$C_{3-8}$ cycloalkyl,
halogen,
nitro,
cyano,
amino which may be unsubstituted or mono- or di-substituted by $C_{1-8}$ alkyl, $C_{3-8}$ cycloalkyl, acyl, trifluoroacyl, aralkyl, aryl or $C_{1-16}$ alkylaminoalcohol, thiol and
a group of the formula —O—C(R)=O, wherein R is selected from the group consisting of
hydrogen,
$C_{1-16}$ alkyl,
$C_{3-8}$ cycloalkyl,
alkoxyalkyl,
aralkyl,
araloxyalkyl,
aryloxyalkyl and
aryl;
$R_6$ and $R_7$ are independently selected from the group consisting of
hydrogen,
halogen,
hydroxyl,
$C_{1-16}$ alkoxyl,
$C_{1-16}$ alkyl,
$C_{2-16}$ acetylenyl, $C_{3-8}$ cycloalkyl,
$C_{2-16}$ alkenyl,
cyano,
mono or oligosaccharides commonly present in anthracyclines, for example one or more sugars selected from rhodosamine, cinerulose-B, L-cinerulose, D-cinerulose, cinerulose-A, amicetose, aculose, rednose, rhodinose, 2-deoxyfucose, daunosamine, acosamine and trifluoroacetyl-daunosamine, a group of the formula —O—C(R)=O, wherein R is selected from the group consisting of
hydrogen,
$C_{1-16}$ alkyl,
$C_{3-8}$ cycloalkyl, and
alkoxyalkyl;
acyl of the formula —C(R)=O, wherein R is selected from the group consisting of
hydrogen,
$C_{1-16}$ alkyl,
$C_{3-8}$ cycloalkyl,
hydroxyalkyl,
alkoxyalkyl,
araloxyalkyl,
acyloxyalkyl,
amino which may be unsubstituted or mono- or di-substituted, and
a naturally occurring amino acid as defined above or a synthetic amino acid;
a group of the formula —C(OR)=O, wherein R is selected from the group consisting of
hydrogen,
$C_{1-16}$ alkyl, and
$C_{3-8}$ cycloalkyl; and
a monosaccharide of the formula

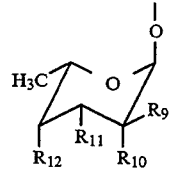

wherein
$R_9$ and $R_{10}$ are independently selected from the group consisting of
hydrogen,
halogen,
hydroxyl,
$C_{1-16}$ alkoxyl,
$C_{1-16}$ alkyl,
$C_{3-8}$ cycloalkyl and
thiol;
$R_{11}$ is selected from the group consisting of
amino,
mono or dibenzylated amino,
acylated amino,
trifluoroacylated amino,
morpholino,
cyano substituted morpholino,
mono-, di-, tri- or tetra-methoxy substituted morpholino,
hydroxyl,
hydrogen,
halogen,
$C_{1-16}$ alkoxyl, $C_{3-8}$ cycloalkyl,
thiol,
chloroalkylnitrosoureido of the formula $NH(CO)N(NO)(CH_2)_nCH_2Cl$, wherein n is 0 to 4,
sulfide and
mono or dialkylated amino with 1 to 16 carbons; and $R_{12}$ is selected from the group consisting of
hydrogen,
hydroxyl or its tetrahydropranyl ether,
halogen,
mono or oligosaccharide commonly present in other anthracyclines, such as those defined above,
amino,
mono or dialkylated amino with 1 to 16 carbons,
$C_{1-6}$ alkoxy,
$C_{3-8}$ cycloalkyl,
benzoate which may be unsubstituted or substituted by nitro, for example p-nitrobenzoate, acetoxy and trifluoroacetoxy;

inclusive of isomers and mixtures thereof, including diastereoisomeric mixtures and racemic mixtures, and the pharmaceutically acceptable salts and metal chelate complexes.

Preferred compounds of formula (11) are those wherein $X_1$ and $X_2$ are independently selected from the group consisting of
O
S
SO
$SO_2$
C=O
NH $X_3$ is selected from the group consisting of
O
S
SO
$SO_2$
$C(R_{13})(R_{14})$, wherein $R_{13}$ and $R_{14}$ are independently selected from the group consisting of
hydrogen
$C_{1-4}$ alkyl
acyl of the formula $-C(R)=O$, wherein R is selected from the group consisting of
hydrogen
$C_{1-8}$ alkyl
hydroxyalkyl,
alkoxyalkyl,
acyloxyalkyl, and
amino which may be unsubstituted or mono- or di-substituted;
a group of the formula $-C(OR)=O$, wherein R is selected from the group consisting of
hydrogen,
$C_{1-8}$ alkyl,
aryl, and
aralkyl;
a group of the formula $-CH_2C(OR)=O$, wherein R is selected from the group consisting of
hydrogen
$C_{1-8}$ alkyl and
amino which may be unsubstituted or mono- or di-substituted;

$R_1$, $R_2$, $R_3$, $R_4$, $R_5$ and $R_8$ are independently selected from the group consisting of
hydrogen,
hydroxyl,
$C_{1-4}$ alkoxyl,
fluorine,
chlorine,
amino, and
a group of the formula $-O-C(R)=O$, wherein R is selected from the group consisting of
hydrogen,
$C_{1-16}$ alkyl and
aryl;

$R_6$ and $R_7$ are independently selected from the group consisting of
hydrogen,
hydroxyl,
$C_{1-8}$ alkoxy,
$C_{2-8}$ alkenyl,
cyano,
a group of the formula $-O-C(R)=O$, wherein R is selected from the group consisting of
hydrogen, and
$C_{1-8}$ alkyl;
acyl of the formula $-C(R)=O$, wherein R is selected from the group consisting of
hydrogen,
$C_{1-8}$ alkyl,
hydroxyalkyl,
alkoxyalkyl,
acyloxyalkyl and
amino which may be unsubstituted or mono- or di-substituted;
a group of the formula $-C(OR)=O$, wherein R is selected from
hydrogen and
$C_{1-8}$ alkyl;
a monosaccharide of the formula

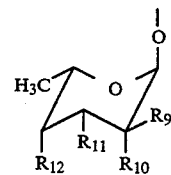

wherein
$R_9$ and $R_{10}$ are independently selected from the group consisting of
hydrogen,
fluorine,
chlorine and
hydroxyl;
$R_{11}$ is selected from the group consisting of
amino,
mono or dibenzylated amino,
acylated amino,
trifluoroacylated amino,
morpholino,
cyano substituted morpholino,
mono-, di-, tri-, or tetra-methoxy substituted morpholino,
hydroxyl,
mono or dialkylated amino with 1 to 16 carbons, chloroalkylnitrosoureido of the formula NH(CO)N(NO)(CH$_2$)$_n$CH$_2$Cl, wherein n is 0 to 4, C$_{1-8}$ alkoxyl and fluorine; and R$_{12}$ is selected from the group consisting of
hydroxyl or its tetrahydropyranyl ether,
halogen,
mono or oligosaccharide commonly present in other anthracyclines, amino,
mono or dimethylated amino,
C$_{1-8}$ alkoxy,
benzoate,
p-nitrobenzoate,
acetoxy and
trifluoroacetoxy, More preferred compounds of the formula (11) are those wherein X$_1$ and X$_2$ are independently selected from the group consisting of
O
S
SO
SO$_2$
C=O X$_3$ is selected from the group consisting of
S
SO
SO$_2$
C(R$_{13}$)(R$_{14}$), wherein R$_{13}$ and R$_{14}$ are independently selected from the group consisting of
C$_{1-4}$ alkyl
acyl of the formula —C(R)=O, wherein R is selected from the group consisting of
methyl
hydroxymethyl,
acyloxymethyl,
amino;
a group of the formula —C(OR)=O, wherein R is selected from the group consisting of
hydrogen,
methyl and
ethyl;
a group of the formula —CH$_2$C(OR)=O, wherein R is selected from the group consisting of
hydrogen
methyl and
ethyl;

R$_2$, R$_2$, R$_3$, R$_4$, R$_5$ and R$_8$ are independently selected from the group consisting of hydrogen, hydroxy, methoxy, amino, and fluorine;

R$_6$ and R$_7$ are independently selected from the group consisting of
hydrogen,
hydroxy,
methoxy,
cyano,
acyl of the formula —C(R)=O, wherein R is selected from the group consisting of
methyl,
hydroxymethyl,
acyloxymethyl,
amino;
acetate,
trifluoroacetate, and
a monosaccharide of the formula

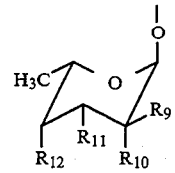

wherein

R$_9$ and R$_{10}$ are independently selected from the group consisting of
hydrogen and
fluorine;

R$_{11}$ is selected from the group consisting of
amino,
dimethylamino,
trifluoroacylated amino,
morpholino,
cyano substituted morpholino,
mono-, di-, tri-, or tetra-methoxy substituted morpholino,
chloroalkylnitrosoureido of the formula NH(CO)N(NO)(CH$_2$)$_n$CH$_2$Cl, wherein n is 0 to 4, and
hydroxyl; and R$_{12}$ is selected from the group consisting of
hydroxyl or its tetrahydropropyranyl ether,
benzoate,
p-nitrobenzoate,
amino and
fluorine.

Further preferred compounds of the formula (11) are those wherein

X$_1$ and X$_2$ are independently selected from the group consisting of
O
S
SO
C=O;

X$_3$ is selected from the group consisting of
S
SO
SO$_2$;

R$_1$, R$_2$, R$_3$ and R$_4$ each independently is hydrogen and fluorine,

R$_5$ and R$_8$ are independently selected from hydrogen and hydroxyl;

R$_6$ and R$_7$ are independently selected from
hydrogen,
hydroxyl,
cyano,
acyl of the formula —C(R)=O wherein R is selected from methyl, hydroxymethyl and amino,
acetate, and
a monosaccharide of the formula

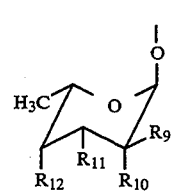

wherein $R_9$ and $R_{10}$ are independently selected from hydrogen and fluorine, $R_{11}$ is selected from amino, dimethylamino, trifluoroacetamido, morpholino, mono-, di- tri- or tetra-methoxy substituted morpholino, chloroalkylnitrosoureido of the formula $NH(CO)N(NO)(CH_2)_nCH_2Cl$, wherein n is 0 to 4, and cyano substituted morpholino, and $R_{12}$ is selected from hydroxy, benzoate and p-nitrobenzoate.

The terms "alkyl" and "alkenyl" as employed herein include both straight and branched chain saturated and ethylenically unsaturated radicals of up to 16 carbons, for example methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the corresponding unsaturated radicals, for example ethylenyl, propylenyl, butenyl and hexenyl, the various branched chain isomers thereof, as well as such groups including one or more halo substituents, such as F, Cl, Br, I or $CF_3$, an alkoxy substituent, an aryl substituent, an alkyl-aryl substituent, a haloaryl substituent, a cycloalkyl substituent or an alkylcycloalkyl substituent.

The term "cycloalkyl" as used herein means a cycloalkyl group having 3 to 8 carbons, for example cyclopropyl, cyclobutyl, cyclopentyl, cyclohexyl, cyclopentylmethyl, cyclohexylmethyl, cyclohexylethyl, cycloheptyl and cyclooctyl.

The term "alkylamine" as used herein refers to an alkyl group as defined above having an amino substituent which may be unsubstituted or mono- or di-substituted by $C_{1-8}$ alkyl, $C_{3-8}$ cycloalkyl, acyl, trifluoroacyl, aralkyl, aryl or thiol.

The term "aryl" as employed herein refers to monocyclic or bicyclic aromatic groups containing from 6 to 10 carbons in the ring portion, such as phenyl, naphthyl, substituted phenyl or substituted naphthyl, wherein the substituent on either the phenyl or naphthyl may be for example $C_{1-4}$ alkyl, halogen, $C_{1-4}$ alkoxy or nitro.

The term "halogen" as used herein means chlorine, bromine, fluorine or iodine.

The term "aralkyl" as used herein refers to alkyl groups as discussed above having an aryl substituent, such as benzyl, p-nitrobenzyl, phenethyl, diphenylmethyl, and triphenylmethyl.

The term "alkoxy" or "aralkoxy" as used herein includes any of the above alkyl or aralkyl groups linked to an oxygen atom.

The term "alkoxyalkyl" as used herein means any alkyl as discussed above linked to any alkoxy as discussed above, for example methoxymethyl.

The term "aryloxyalkyl" as used herein means any alkyl as discussed above linked to an aryl as discussed above by an oxygen atom, for example phenoxymethyl.

The term "araloxyalkyl" as used herein means an aralkyl as discussed above linked to an alkyl as discussed above by an oxygen atom, for example benzyloxymethyl.

The term "acyloxyalkyl" as used herein means a $C_{1-8}$ acyl group linked to an alkyl group as discussed above by an oxygen atom, for example acetoxymethyl.

The term "hydroxyalkyl" as used herein means an alkyl group as discussed above bonded to a hydroxyl group, for example hydroxymethyl.

This invention includes all the possible isomers and mixtures thereof, including diastereoisomeric mixtures and racemic mixtures, resulting from the possible combination of R or S stereochemical centers, when pertinent, at the three possible non-aromatic atomic positions of the A ring as well as in all the chiral centers present in the sugar moiety.

This invention also comprises novel compounds which are prepared as intermediates or precursors of compounds of formula (11). Such intermediate compounds are described hereinafter in connection with processes for the preparation of compounds of formula (11).

Some of the compounds of formula (11) can be prepared by the process illustrated in Reaction Scheme I.

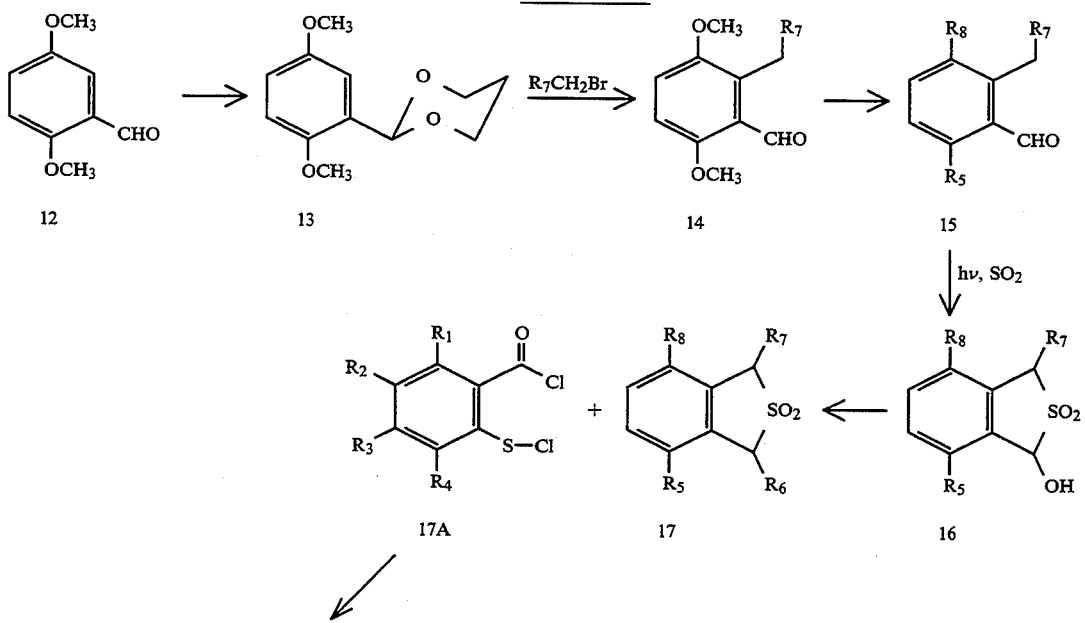

SCHEME I

-continued
SCHEME I

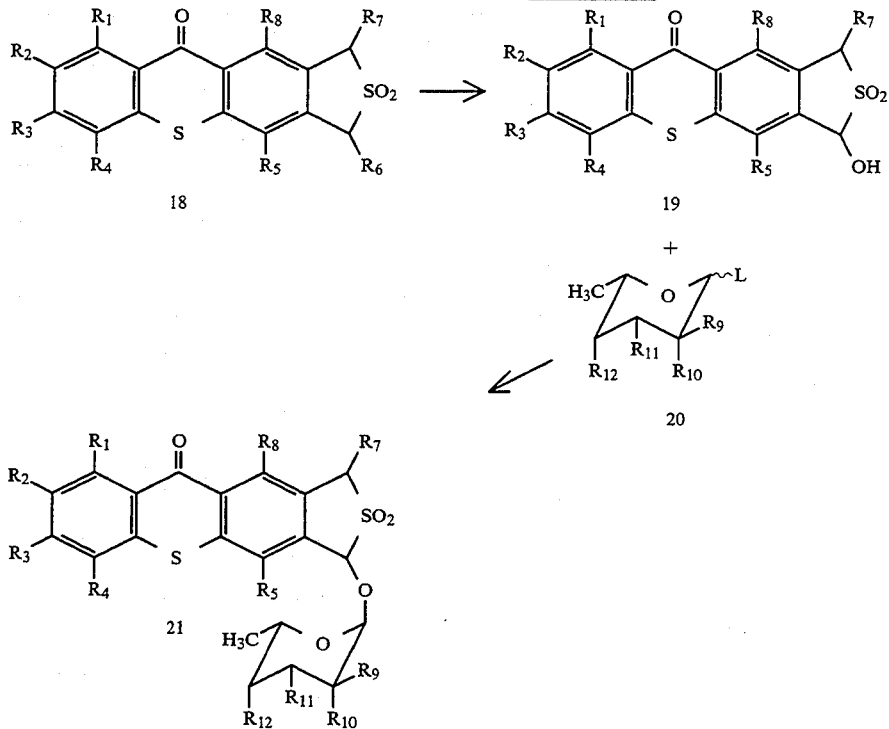

With reference to Reaction Scheme I, 2,5-dimethoxybenzaldehyde dioxane acetal (13) can be prepared by treating at reflux 2,5-dimethoxybenzaldehyde (12) with 1,3-propanediol in benzene or any other suitable solvent and with an acid catalyst such as p-toluenesulfonic acid. The dioxane acetal (13) can then be treated with an alkyl lithium and the lithio salt reacted with an appropriate alkyl halide of the formula $R_7CH_2X$, wherein X is halogen and $R_7$ is as defined above. Subsequent aqueous acidic treatment can lead to an appropriate 2,5-dimethoxy-6-alkylbenzaldehyde such as (14). The dimethoxy substituents in intermediate (14) can then be converted to a large variety of organic functionalities $R_5$ and $R_8$ as defined above by employing methodology which is well known to the one familiar with the art of organic synthesis. For example, the treatment of a compound such as (14) with an aluminum chloride/sodium chloride melt at 150° to 180° C., followed by acidic treatment, can give an hydroquinone intermediate in which the phenoxy moieties can then be transformed to a large number of side chains by using common organic procedures to give compounds of general formula (15). Photochemical irradiation of an intermediate such as (15) in a solution of $SO_2$ in an aryl solvent such as benzene can give a dihydrothiophene-2,2-dioxide of formula (16) in which the hydroxyl functionality can then be converted to various $R_6$ substituents as defined above by employing simple organic procedures commonly available to the organic chemist, hence, to yield synthetic intermediates of general formula (17). A double Friedel-Crafts addition of intermediates of formula (17A) (Honek, J. F., Doctoral Disertation, McGill University, Dept. of Chemistry, Montreal, Quebec, Canada, 1983)) to intermediates of formula (17) in an organic solvent such as 1,2-dichloroethane or dichloromethane with a Lewis acid such as tin tetrachloride or aluminum trichloride can then give the desired ring A and C heteroaromatic tetracycle of general formula (18).

The corresponding glycosides of general formula (21) are best prepared through the intermediacy of aglycones such as (19). These latter compounds are readily available from (18), for example, the treatment of thioxanthyl sulfonyl intermediates (18) with an acetate for an $R_6$ substituent with a base such as sodium hydroxide in a tetrahydrofuran-water solvent system can yield the necessary glycone of general formula (19).

An aglycone of formula (19) is reacted with a sugar derivative of formula (20) in which $R_9$ to $R_{12}$ are as defined herein and L is a displaceable atom or group. Suitable groups L include halogen, for example iodine, bromine or chlorine, an unsubstituted or substituted benzoyl group such as p-nitrobenzoyl, or —OR where R is an unsubstituted or substituted alkyl group e.g. a $C_{1-16}$ alkyl group such as methyl, ethyl or butyl, or R is an unsubstituted or substituted acyl group, e.g. a $C_{1-16}$ acyl group such as acetyl, or R is an unsubstituted or substituted aryl group. Such sugars are obtained by derivatizing known saccharides of the family of anthracycline antibiotics which are available from commercial or natural sources, (see, for example, Monneret, C., Martini, A., Pais, M., Carbohydrate Research, 166, 59–70, 1987 and references therein; Acton, E. M., Tong, G. L. Mosher, C. W., and Wolgemuth, R. L., J. Med. Chem. 27, 638–645, 1984 and references therein; Arcamone F., Cancer Research, 45, 5995–5999, 1985 and references therein).

The aglycone of formula (19) is typically reacted with the appropriate sugar derivative of formula (20) in a compatible solvent such as methylene chloride using a Lewis acid such as titanium tetrachloride, stannic chloride, or trimethylsilytrifluoromethanesulfonate to give glycosides such as (21). Alternatively, as is known in the art of anthracycline chemistry, when the leaving group of the sugar moiety is a halogen, the Koenigs-Knorr glycosidation or its modification may be used.

A more general approach for the preparation of compounds of general formula (11) is illustrated in reaction Scheme II.

(24). For example, the reaction of (23) with a base such as sodium or potassium hydroxide in the presence or absence of sodium hydride or lithium diisopropylamide or other non-nucleophilic base in a suitable solvent such as tetrahydrofuran, diglyme, dimethylformamide, ace-

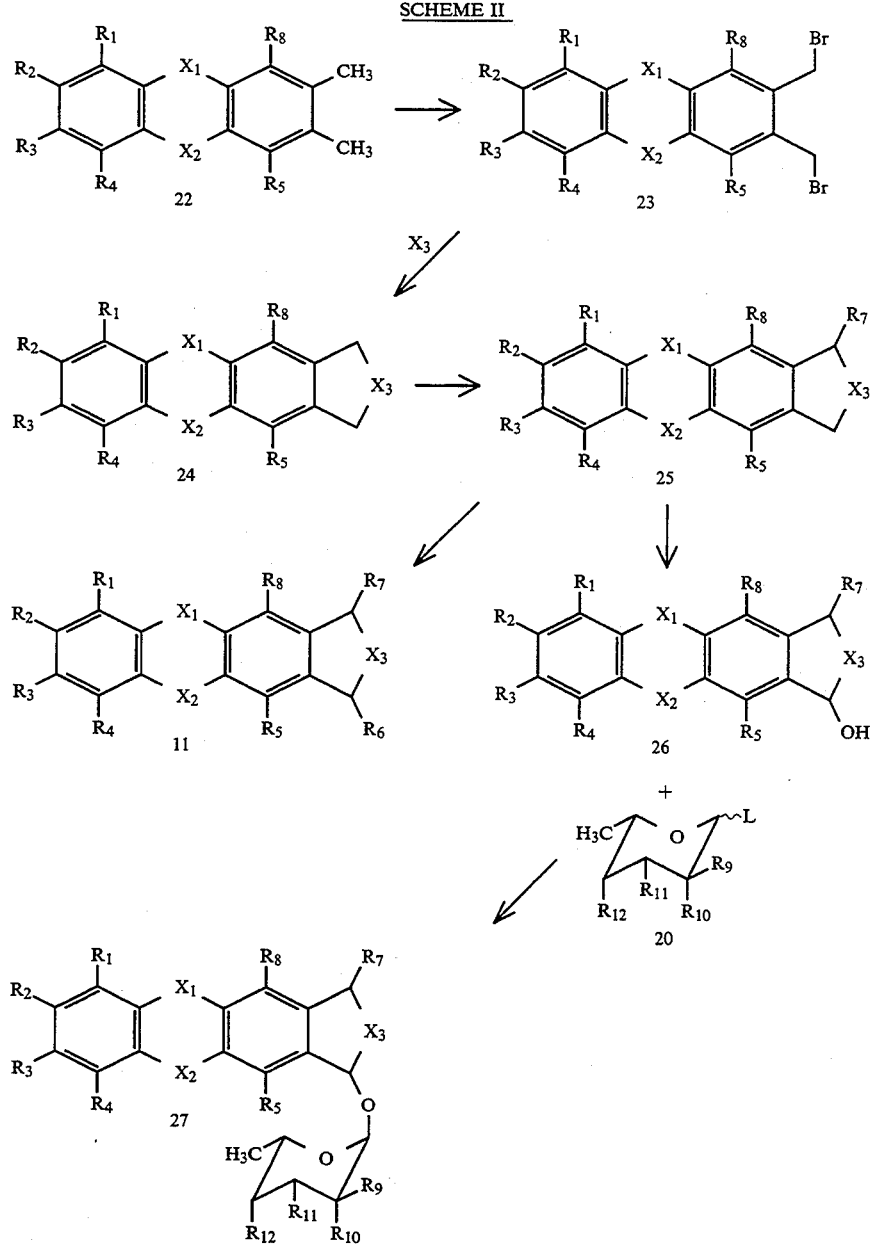

SCHEME II

With reference to Scheme II, the tricyclic compound of formula (22) can be obtained from the chemical transformation of the corresponding 2,3-demethylated tricyclic compounds using methods which are well known to the one familiar with the art of organic synthesis. Free radical bis-bromination of compounds of formula (22) with a brominating agent such as n-bromosuccinamide or bromine with the aid of light, azobisisobutyronitrile AIBN, or a peroxide such as t-butyl peroxide for free radical initiation can give the tricyclic dibromomethyl derivative of formula (23). The addition of appropriately functionalized nucleophiles of the formula $X_3$ as defined above to the dibromomethyl intermediate (23) can lead to the tetracyclic derivative of formula tone, or diethylether can give a tetracycle with a furan ($X_3$=O) as the A ring.

Alternatively, treatment of (23) with sodium sulfide can give a tetracyclic intermediate of formula (24) ($X_3$=S) which can then be oxidized to a thiophene oxide ($X_3$=SO) or a thiophene dioxide ($X_3$=SO$_2$) by using an oxidizing agent such as hydrogen peroxide, m-chloroperbenzoic acid or periodic acid. The addition of ammonia to intermediates such as (23) can lead to compounds with $X_3$=NH in general formula (24). Compounds of formula (24) and which contain the moiety $X_3$=C($R_{13}$)($R_{14}$) can be obtained via the addition of an appropriately functionalized carbon nucleophile to compounds of formula (23), for example, the nucleophilic addition to (23) of NC—CH$_2$—OR under basic conditions achieved through the use of bases such as sodium hydroxide, lithium diisopropylamide or potassium t-butoxide in an adequate aprotic solvent can yield tetracycles of formula (24) with X$_3$=C(CN)OR, which can further be converted hydrolytically to other compounds of formula (24) but with X$_3$=C=O. These latter derivatives upon reduction for example with hydrazine could then lead to nor-heteroanthracyclines with X$_3$=CH$_2$.

The versatility of intermediates of formula (23) can further be illustrated as follows. The addition of the carbon nucleophile of CH$_3$COCH$_2$COO C(CH$_3$)$_3$ having been generated with a strong base, such as sodium hydride, to intermediates of formula (23) can give, after acidic treatment, tetracycles of formula (24) with X$_3$=CHCOCH$_3$. The reaction of (23) with CH$_3$O-COCH$_2$CO$_2$CH$_3$ under strongly basic conditions, conveniently attained with sodium hydroxide or sodium t-butoxide, can lead to compounds of formula (24) with X$_3$=C(CO$_2$CH$_3$)$_2$ which can be further transformed to compounds of structure (24) with X$_3$=CHCO$_2$CH$_3$ after decarboxylation or to other intermediates of formula (24) with X$_3$=C(CH$_2$OH)$_2$. Other derivatives (X$_3$=C(SO$_2$phenyl)OR with structure (24) can be obtained by reacting (23) with CH$_2$(SO$_2$phenyl)OR under basic conditions in aprotic media. These latter intermediates can then be desulfurized to give products in which X$_3$=CHOR in (23) or can be reduced with a reagent such as triphenylphosphine to yield tetracyclic compounds of formula (24) with X$_3$=C(SR)OR.

The versatile approach to convert formula (23) into (24) discussed above is not intended to be limiting. Carbon based X$_3$ substitutes are accessible through the use of organic methods available to one familiar in the art of organic synthesis.

Transformation of compounds of formula (24) into (25) can be accomplished by monobrominating under free radical conditions intermediates (24) with N-bromosuccinimide or bromine in a solvent such as carbon tetrachloride with light, t-butylperoxide or AIBN for initiation. Subsequent treatment with a nucleophile R$_7$$^-$ can give compounds of formula (25) which could be further transformed to more complex analogs, for example R$_7$=CN into COCH$_3$ or R$_7$=C≡CH into COCH$_2$OH, by using published methods available to the organic chemist. The target compounds of formula (11) an be obtained from (26) by repeating the procedure described above for the conversion of (24) into (25). As discussed previously for reaction Scheme I, the glycosides of formula (27) can be prepared by coupling known sugars of formula (20) with aglycones such as (26). These latter derivatives can be prepared by brominating derivative such as (25) with n-bromosuccinimide or bromine in carbon tetrachloride in the presence of light, AIBN or a peroxide for initiation, followed by solvolysis in a solvent system such as THF/water or dioxane/water.

It will be appreciated that the heteroanthracyclines of formula (27) can further be transformed to a variety of structures by using synthetic methodologies well understood in the art of anthracycline chemistry.

It will also be appreciated that the reactions described herein may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g. benzyl), acyl or aryl (e.g. 2,4-dinitrophenyl), subsequent removal of the protecting group being effected when desired by hydrolysis or hydrogenolysis as appropriate using standard conditions. Hydroxyl groups may be protected using any conventional hydroxyl protecting group, for example, as described in "Protective Groups in Organic Chemistry", Ed. J. F. W. McOmie (Plenum Press, 1973) or "Protective Groups in Organic Synthesis" by Theodora W. Greene (John Wiley and Sons, 1981). Examples of suitable hydroxyl protecting groups include groups selected from alkyl (e.g. methyl, t-butyl or methoxymethyl), aralkyl (e.g. benzyl, diphenylmethyl or triphenylmethyl), heterocyclic groups such as tetrahydropyranyl, acyl, (e.g. acetyl or benzoyl) and silyl groups such as trialkylsilyl (e.g. t-butyldimethylsilyl). The hydroxyl protecting groups may be removed by conventional techniques. Thus, for example, alkyl, silyl, acyl and heterocyclic groups may be removed by solvolysis, e.g. by hydrolysis under acidic or basic conditions. Aralkyl groups such as triphenylmethyl may be similarly removed by solvolysis, e.g. by hydrolysis under acidic conditions. Aralkyl groups such as benzyl may be cleaved, for example, by treatment with BF$_3$/etherate and acetic anhydride followed by removal of acetate groups.

In the above processes, the compounds of formula (11) are generally obtained as a mixture of diastereoisomers. These isomers may be separated by conventional chromatography or fractional crystallization techniques.

Where the compound of formula (11) is desired as a single isomer, it may be obtained either by resolution of the final product or by stereospecific synthesis from isomerically pure starting material or any convenient intermediate.

Resolution of the final product, or an intermediate or starting material therefor, may be effected by any suitable method known in the art: see for example, "Stereochemistry of Carbon Compounds", by E. L. Eliel (McGraw Hill, 1962) and "Tables of Resolving Agents", by S. H. Wilen.

The compounds of the formula (11) possess in vitro anti-cancer and anti-tumor activity. While it is possible to administer one or more of the compounds of the invention as a raw chemical, it is preferred to administer the active ingredient(s) as a pharmaceutical composition.

In another aspect, the invention therefore provides pharmaceutical compositions primarily suitable for use as in vitro antitumor and anticancer agents, comprising an effective amount of at least one compound of the invention or a pharmaceutically acceptable dervative thereof in association with one or more pharmaceutically acceptable carriers and optionally other therapeutic and/or prophylactic ingredients. All the pharmaceutically acceptable salts for example the HCl and tartaric acid salts of the compounds useful as in vitro antitumor agents, are included in this invention.

It will be appreciated by those familiar with the art of clinical oncology that the compound(s) of this invention can be used in combination with other therapeutic agents, including chemotherapeutic agents (Cancer: Principles and Practices of Oncology, 3rd Edition, V. T. DeVito Jr., S. Hellman and S. A. Rosenberg; Antineoplastic Agents edited by W. A. Remers, John Wiley and Sons, N.Y., 1984). Thus, it will be understood that the compounds or pharmaceutical compositions of the invention may be formulated with the therapeutic agent to form a composition and administered together or the compounds or compositions and the therapeutic agent may be administered separately, as appropriate for the medical condition being treated.

Therefore, for therapeutic purposes, a compound or composition of this invention can be used in association with one or more of the therapeutic agents belonging to any of the following groups:

1) Alkylating agents such as:
   2-haloalkylamines (e.g. melphalan and chlorambucil);
   2-haloalkylsulfides;
   N-alkyl-N-nitrosoureas (e.g. carmustine, lomustine or semustine);
   aryltriazines (e.g. decarbazine);
   mitomycins (e.g. mitomycin C);
   methylhydrazines (e.g. procarbazine);
   bifunctional alkylating agents (e.g. mechlor-ethamine);
   carbinolamines (e.g. sibiromycin);
   streptozotocins and chlorozotocins;
   phosphoramide mustards (e.g. cyclophosphamide);
   urethane and hydantoin mustards
2) Antimetabolites such as:
   mercaptopurines (e.g. 6-thioguanine and 6-(methylthio)purine);
   azapyrimidines and pyrimidines;
   hydroxyureas;
   5-fluorouracil
   folic acid antagonists (e.g. amethopterin);
   cytarabines;
   prednisones;
   diglycoaldehydes
3) Intercalators such as:
   bleomycins and related glycoproteins;
   anthracylines (e.g. doxorubicin, daunorubicin, epirubicin, esorubicin, idarubicin, aclacinomycin A);
   acridines (e.g. m-AMSA);
   hycanthones;
   ellipticines (e.g. 9-hydroxyellipticine);
   actinomycins (e.g. actinocin);
   anthraquinones (e.g. 1,4-bis[(aminoalkyl)amino]-9,10-anthracenediones);
   anthracene derivatives (e.g. pseudourea and bisanthrene);
   phleomycins;
   aureolic acids (e.g. mithramycin and olivomycin);
4) Mitotic inhibitors such as:
   dimeric catharanthus alkaloids (e.g. vincristine, vinblastine and vindesine);
   colchicine derivatives (e.g. trimethylcolchicinic acid)
   epipodophyllotoxins and podophylotoxins (e.g. etoposide and teniposide);
   maytansinoids (e.g. maytansine and colubrinol);
   terpenes (e.g. helenalin, tripdiolide and taxol);
   steroids (e.g. 4$\beta$-hyroxywithanolide E);
   quassiniods (e.g. bruceantin);
   pipobroman;
   methylglyoxals (e.g. methylglyoxalbis(thiosemicarbazone);
5) Hormones (e.g. estrogens, androgens, tamoxifen, nafoxidine, progesterone, glucocorticoids, mitotane, prolactin);
6) Immunostimulants (e.g. human interferons, levamisole and tilorane);
7) Monoclonal and polyclonal antibodies;
8) Radiosensitizing and radioprotecting compounds (e.g. metronidazole and misonidazole);
9) Other miscellaneous cytotoxic agents such as:
   camptothecins;
   quinolinequinones (e.g. streptonigrin and isopropylidene azastreptonigrin);
   cisplatin and related platinum complexes;
   tricothecanes (e.g. trichodermol or vermicarin A);
   cephalotoxines (e.g. harringtonine);
10) Cardioprotecting compounds, such as ($\pm$)-1,2-bis(3,5-dioxopiperazin-1-yl) propane, commonly known as ICRF-187, and ICRF-198;
11) Drug-resistant reversal compounds such as P-glycoprotein inhibitors, for example Verapamil; and
12) Cytotoxic cells such as lymphokine activated killer cells or T-cells.

The above list of possible therapeutic agents is not intended to limit this invention in any way.

The pharmaceutical compositions of the invention can be in forms suitable for oral, rectal, nasal, topical (including buccal and sub-lingual), vaginal or parenteral (including intramuscular, subcutaneous and intravenous) administration by inhalation or by insufflation. Where appropriate, the formulations may be conveniently presented in discrete dosage units and may be prepared by any method well known in the art of pharmacy. All methods include the step of bringing into association the active compound with liquid carriers or finely divided solid carriers or both and then, if necessary, shaping the product into the desied formulation.

For injectable use, the pharmaceutical composition forms include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, dimethyl sulfoxide (DMSO), propylene glycol, and liquid polyethylene glycol, and the like suitable mixtures thereof, and vegetable oils. The proper fluidity can be maintained for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorocutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient or ingredients in the required amount in the appropriate solvent with various of the other ingredients enumerated above, as required followed by filtered sterilation. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

As used herein, the expression "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except isofar as any conventional media or agent is incompatible with the active ingredient, its use in the present compositions is contemplated. Supplementary active ingredients can be incorporated into the inventive compositions.

It is especially advantageous to formulate compositions in dosage unit form for ease of administration and uniformity of dosage. Dosage unit form as used in the specification and claims herein refers to physically discrete units suited as unitary dosages for the animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated; the particular condition and its severity; the particular form of the active ingredient, the potency of the active ingredient, and the route of administration. A daily dose of from about 0.01 to about 100 mg/kg of body weight given singly or in divided doses of up to 5 times a day or by continuous infusion embraces the effective range for the treatment of most conditions for which the novel compounds are effective and substantially non-toxic. For a 75 kg subject, this translates into between about 0.75 and about 7500 mg/day. If the dosage is divided for example, into three individual dosages, these will range from about 0.25 to about 2500 mg. of the active ingredient. The preferred range is from about 0.1 to about 50 mg/kg of body weight/day with about 0.2 to about 30 mg/kg of body weight/day being more preferred.

The principal active ingredient is compounded for convenient and effective administration in effective amounts with a suitable pharmaceutically-acceptable carrier in dosage unit form as hereinbefore disclosed. A unit dosage form can, for example, contain the principal active ingredient in amounts ranging from about 0.1 to about 1000 mg., with from about 1.0 to about 500 mg. being preferred. Expressed in proportions, the active ingredient is generally present in from about 0.1 to about 500 mg/ml of carrier. In the case of compositions containing supplementary active ingredients, the dosages are determined by reference to the usual dose and manner of administration of the said ingredients.

Antitumor treatment comprises the administration of any of the compounds of this invention in an acceptable pharmaceutical formulation at the effective therapeutic dosage. It is understood that chemotherapy can require the use of any of the compounds of this invention bound to an agent which facilitates targeting the compound to the tumor cells. The agent may be chosen from, for example, monoclonal or polyclonal antibodies, proteins and liposomes. The compounds of this invention could also be administered as monomeric, dimeric or oligomeric metal chelate complexes with, for example iron, magnesium or calcium.

The compounds of the invention exhibit in vitro antitumor or anticancer activity, most notably, antitumor or anticancer activity with human breast cancer, leukemia, colon cancer, lung cancer, renal cancer, ovarian cancer, CNS cancer and melanoma.

Certain of the above-described intermediates employed in the synthesis of compounds of the invention are also of interest from a pharmacological standpoint. As with the compounds (11), the intermediates are preferably administered as a pharmaceutical composition for the treatment of the conditions listed above, and may be administered in the dosages noted above for the compounds (11). Moreover, the intermediates may be administered as pharmaceutically acceptable salts or as metal chelate complexes where appropriate, and may be administered in admixture with other of the intermediates compounds, and/or with compounds of the formula (11), and/or with one or more of the therapeutic agents or agents targeting cancer or tumor cells.

EXAMPLES

The invention will now be described with reference to Scheme III in the following non-limiting examples. All temperatures are in degrees Celsius.

SCHEME III
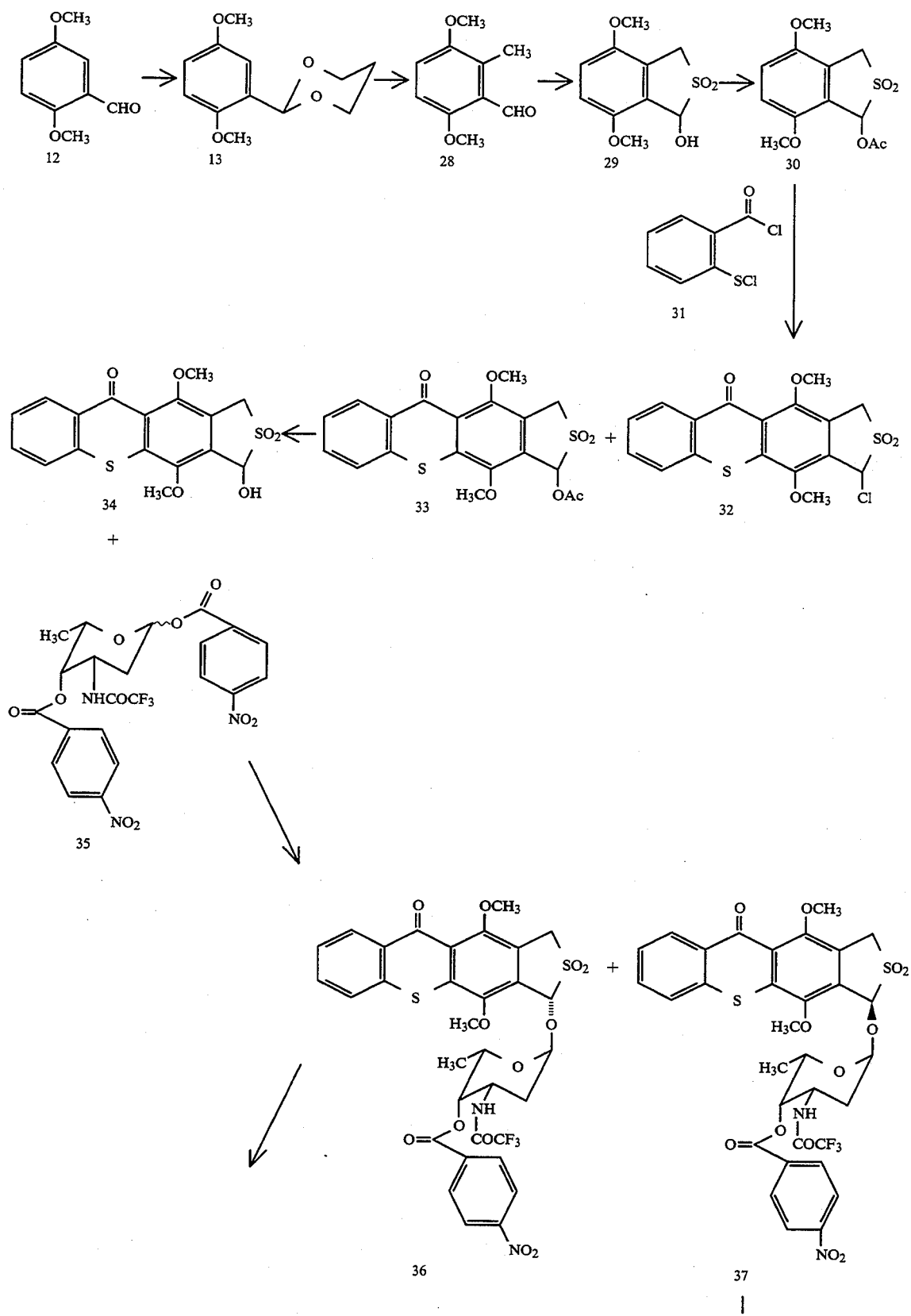

-continued
SCHEME III

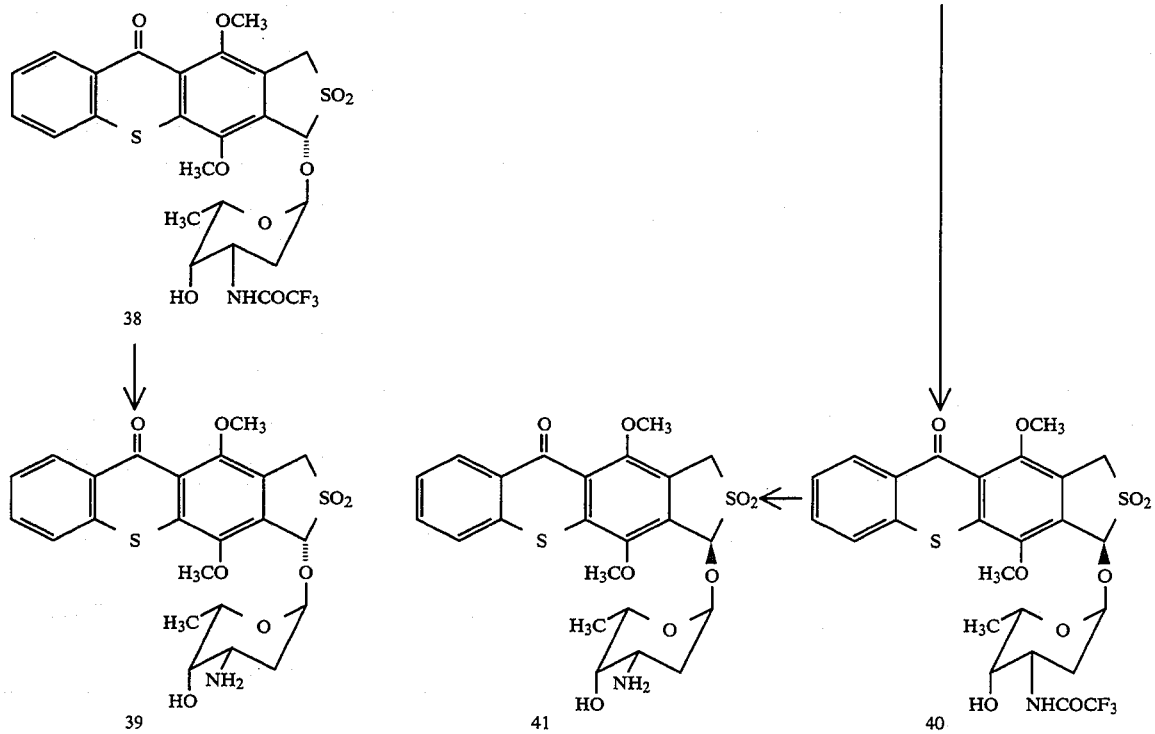

EXAMPLE 1

4,11-Dimethoxy-1-hydroxy-5-oxo-5-H-1,3-dihydrothioxantheno[2,3-c] thiophene-2,2-dioxide (34)

Step 1: 2,5-Dimethoxybenzaldehydedioxane acetal (13)

A solution containing 200 g (1.2 mole) of 2,5-dimethoxybenzaldehyde (12), 150 g (2.0 mole) of 1,3-propanediol, and 1.0 g of p-toluenesulfonic acid in 1.0 l of benzene was refluxed until no more water could be isolated in the Dean-Stark water separator (6 hours). The reaction mixture was then cooled and washed with 400 ml of saturated aqueous sodium bicarbonate, 200 ml of water and 200 ml of saturated aqueous sodium chloride. The organic layer was then dried over MgSO4 and the solvent was removed in vacuo. Distillation of the residue under reduced pressure (B.P. 167° C. at 1 mmHg) gave 263.7 g (98% yield) of a slightly yellow oil characterised as 2,5-dimethoxybenzaldehydedioxane acetal (13). $^1$H NMR (200 MHz,CDCl$_3$) δ:1.40 (d m,1H,HCHa), 2.24 (m,1H,HCHe), 3.77 (s,3H,OCH$_3$), 3.78 (s,3H, OCH$_3$), 4.00 (dt,2H,O— HCHa), 4.24 (dd,2H,O—HCHe), 5.84 (s,1H,O—CH—O), 6.82 (dd,2H,ArH), 7.19 (d,1H,ArH).

Step 2: 2,5-Dimethoxy-6-methylbenzaldehyde (28)

To a cooled (−40° C.) solution containing 84.0 g (0.37 mole) of 2,5-dimethoxybenzaldehydedioxane acetal (13) in 2.0 l of dry diethylether was added with stirring and under argon 240 ml of a 2.5M n-butyl lithium solution in hexane. The mixture was stirred for four hours at −25° C. and then 24 hours at −10° C. Then to the cooled (−25° C.) stirred reaction mixture under argon was added 90.0 g of methyl iodide and stirred overnight at room temperature. The solution was then washed twice with 300 ml of water, once with 300 ml of saturated sodium chloride and dried over MgSO4. The organic solvent was evaporated and the residue was dissolved in 500 ml of ether and stirred for 1-½ hours with 500 ml of 1N aqueous HCl. The organic layer was separated and washed twice with 200 ml water, once with 200 ml of brine and dried over MgSO4. Evaporation of the solvent gave a yellow oil which was flash chromatographed with 2.5% ethyl acetate in toluene. A 67% yield (45 g) of 2,5-dimethoxy-6-methylbenzaldehyde (28) was obtained (MP: 61°-61.5° C.). $^1$H NMR (200 MHz, CDCl$_3$) δ:2.46 (s,3H,CH$_3$), 3.78 (s,3H,OCH$_3$), 3.83 (s,3H,OCH$_3$), 6.90 (dd,2H,ArH), 10.58 (s,1H,CHO).

Step 3: 4,7-dimethoxy-1-hydroxy-1,3-dihydrobenzo [c] thiophen-2,2-dioxide (29)

Procedure 1

Under an argon atmosphere, a deoxygenated solution containing 1.60 g (8.9 mmole) of 2,5-dimethoxy-6-methylbenzaldehyde (28), 11.0 g of SO$_2$ in 100 ml of thiophene free benzene was irradiated at 350 nm for 36 hours. The precipitated crystals (2.01 g 93% yield) were filtered and found sufficiently pure for further use.

Procedure 2

For larger scale, under argon, a deoxygenated solution containing 10.0 g (55.5 mmole) of 2,5-dimethoxy-6-methylbenzaldehyde, 50 g of SO$_2$ in 600 ml of thiophene free benzene was irradiated with a medium pressure mercury immersion lamp with pyrex filtration for four days. The resulting sludge was extracted three times with 400 ml of 1N NaOH and the combined aqueous layer was washed twice with 200 ml of methylene chloride. The aqueous layer was then neutralised with concentrated aqueous HCl and the resulting mixture was then extracted three times with 500 ml of methylene chloride. The combined organic layer was then washed once with 200 ml water, 200 ml of saturated aqueous sodium bicarbonate, 200 ml of water, 200 ml of brine, and then dried over MgSO$_4$. Following evaporation of solvent, 11.2 g (83%) of pure 5,8-dimethoxy-1-hydroxy-1,3-dihydrobenzo [c] thiophene-2,2-dioxide (29) was obtained (MP: 140° C. decomposes) $^1$H NMR (200 MHz,CDCl$_3$) δ:3.57 (s,3H,OCH$_3$), 3.60 (s,3H,OCH$_3$), 4.44 (dd,2H, CH$_2$), 5.65 (s,1H,CH), 6.85 (dd,2H,ArH).

Step 4: 4,7-Dimethoxy-1-acetoxy-1,3-dihydrobenzo [2,3-c] thiophene-2,2-dioxide (30)

To a stirred suspension containing 2.928 g (12 mmol) of hydroxysulfone (29) in 200 ml of acetic anhydride was added one drop of concentrated sulfuric acid. Stirring was continued for four hours under argon, the precipitate was filtered, then washed with water and air dried. Flash chromatography from 10% ethyl acetate in toluene of the precipitate gave the acetoxysulfone in 87% yield (2.98 g). MP:227.5°–228.5° C. (decomposes). $^1$H NMR (200 MHz, CDCl$_3$) δ:2.23 (s, 3H, COCH$_3$), 3.82 (s, 6H, 2XOCH$_3$), 4.27 (dd, 2H, J=16.5 Hz,CH$_2$), 6.72 (s, 1H, CH), 6.9 (dd, 2H, J=9.7 Hz, ArH). CMR (75.44 MHz, CDCl$_3$) δ:20.4, CH$_3$; 51.0, CH$_2$; 52.2, 55.9, ArOCH$_3$; 103.8, CH; 111.0, 113.2, aryl CH; 121.9, 122.6, 151.4, 151.6, aryl C; 169.1, C=O. IR (KBr) V$_{Max}$: 1758, ester C=O; 1323, 1190, SO$_2$. MS (EI, 70 eV, 60° C.) m/e: 286 (2.3, M+.), 255 (3, M+.—OCH$_3$) 222 (16, M+.—SO$_2$), 194 (24, M+.—SO$_2$—C$_2$H$_4$O). HRMS calculated for C$_{10}$H$_{14}$O$_6$S: [M+.] 286.0511 found 286.0507.

Step 5: 4,11-Dimethoxy-1-acetoxy-5-oxo-5-H-1,3-dihydrothioxantheno [2,3-c] thiophene-2,2-dioxide (33) and 4,11-Dimethoxy-1-chloro-5-oxo-5-H-1,3-dihydrothioxantheno [2,3-c] thiophene-2,2-dioxide (32)

Following a modification of Honek's procedure (supra), 1.37 g (4.8 mmol) of benzosulfone acetate (30) prepared as above was added under argon to a solution containing 1.91 g (9.4 mmol) of o-chlorosulfenyl benzoylchloride (31) and 5.0 ml of SnCl$_4$ in 25 ml of dichloromethane. After stirring at room temperature for 24 hours, the mixture was thrown in 50 g of ice, diluted with 100 ml of dichloromethane, and the separated organic phase was washed consecutively with 50 ml aliquots of water, saturated sodium bicarbonate, water, brine, and then dried over MgSO$_4$. After evaporation of solvent, flash chromatography of the residue (ethylacetate-toluene) gave the starting material (165 mg, 12% yield), as well as the following compounds:

Thioxanthone (33) (282 mg, 14% yield) MP:190°–195° C. decomposes. $^1$H NMR (200 MHz, CDCl$_3$), δ:2.29 (s, 3H, CH$_3$), 3.97 (s, 3H, OCH$_3$), 4.01 (s, 3H, OCH$_3$), 4.47 (dd, 2H, J=16.0 Hz, CH$_2$), 6.83 (s, 1H, CH), 7.60 (m, 3H, ArH), 8.47 (d, 1H, J=6.0 Hz, ArH). CMR (75.44 MHz, CDCl$_3$) δ:20.4, CH$_3$; 51.9, CH$_2$; 62.1, 62.2, OCH$_3$; 82.1, CH; 126.0, 127.0, 129.6, 132.6, aryl CH; 124.9, 125.6, 127.6, 130.7, 134.9, 135.1, 149.3, 155.2, aryl C; 168.5, ester C=O; 179.9, thioxanthone C=O. IR (ft, CDCl$_3$) V$_{MAX}$: 1766, ester C=O); 1645, thioxanthyl C=O. MS (EI, 70 eV, 225° C.) m/e: 420 (41, M+.), 356 (62, M+—SO$_2$), 313 (56, M+—SO$_2$—C$_2$H$_3$O).

Thioxanthone (32) (218 mg, 11% yield) MP: 242°–244° C. decomposes. $^1$H NMR (200 MHz, CDCl$_3$) δ:4.00 (s, 3H, OCH$_3$), 4.15 (s, 3H, OCH$_3$), 4.56 (dd, 2H, J=15.5 Hz, CH$_2$), 5.94 (s, 1H, CHCl), 7.63 (m, 3H, ArH), 8.49 (dd, 1H, J=1.6, 7.9 Hz, ArH). IR (KBr) V$_{Max}$: 1650, thioxanthone C=O; 1323, 1190, SO$_2$; 810, C—Cl. MS (EI, 70 eV, 230° C.) m/e 396 (49, M+.), 332 (59, M+—SO$_2$).

The respective (1R) and (1S) stereoisomers can be obtained using conventional techniques.

Step 6: 4,11-Dimethoxy-1-hydroxy-5-oxo-5-H-1,3-dihydrothioxantheno [2,3-c] thiophene-2,2-dioxide (34)

Procedure A

A solution containing 425 mg (1.0 mmol) of 1-acetoxythioxanthosulfone (33), prepared as above, in 50 ml of tetrahydrofuran was stirred at room temperature with 15 ml of 1M aqueous NaOH for five minutes. The reaction mixture became cloudy at first but gradually turned yellow. The mixture was then diluted with 150 ml of water, extracted twice with dichloromethane to remove organic impurities, and the organic layers were discarded. The aqueous layer was then neutralized with 12M HCl and re-extracted three times with 100 ml of dichloromethane. The combined organic layers were washed successively once with 50 ml of water, 50 ml of brine, and then dried over MgSO$_4$. Evaporation of solvent gave 375 mg (99% yield) of 1-hydroxythioxanthosulfone (34). MP: 148°–150° C. decomposes. $^1$NMR (200 MHz, CDCl$_3$) δ:3.36 (broad s, 1H exchangeable, OH), 3.82 (s, 3H, OCH$_3$), 4.03 (s, 3H, OCH$_3$), 4.54 (bs, 2H, CH$_2$), 5.83 (bs, 1H, CH), 7.57 (bt, 1H, ArH), 7.80 (m, 2H, ArH), 8.32 (bd, 1H, J=8.1 Hz). IR (FT,CDCl$_3$) V$_{MAX}$: 3350–3600, bs, OH; 1676, thioxanthone C=O; 1289, 1183, SO$_2$.

Procedure B

The same procedure as described above but carried out with 147 mg (3.7 mmol) of 1-chlorothioxanthosulfone (32) gave 118 mg (76% yield) of compound (34).

The respective sterioisomers (1R) and (1S) of compound (34) are obtained using conventional techniques.

EXAMPLE 2

(1S) and (1R) 1-(4'-O-p-nitrobenzoyl-N-trifluoroacyl daunosamine)-4,11-dimethoxy-5-oxo-5-H-1,3-dihydrothioxantheno [2,3-c] thiophene-2,2-dioxide (36) and (37)

Following a modification of the procedure of Kimura et al, Chemistry Letters, 501 (1984), 0.70 ml (2.6 mmol) of trimethylsilyl trifluoromethane sulfonate was added dropwise, at −25° C. and under argon, to a mixture containing 0.70 g (1.3 mmol) of protected daunosamine (35), 1 g of 4A molecular sieves in 100 ml of a 1:3 ether/-dichloromethane solvent system. After stirring at −5° C. for one hour, the mixture was cooled to −10° C., and a solution containing 400 mg (1.1 mmol) of thioxanthone (34) in 50 ml of dichloromethane was transferred under argon over one minute. The resulting mixture was stirred overnight and then added to 100 ml of a 1:1 saturated aqueous sodium bicarbonate-ethylacetate solvent system. The organic phase was separated and the aqueous layer was extracted twice with 50 ml of dichloromethane. The combined organic layer was washed successively with 100 ml of water, 100 ml of brine and then dried over MgSO. Evaporation of solvents yielded a yellow residue which was flash chromatographed with 10% ethylacetate in toluene. The first collected fraction (39% yield) is arbitrarily assigned as compound (36). (MP: 140°–144° C. decomposes). $^1$H NMR (200 MHz, CDCl$_3$) δ:1.22 (d. 3H, J=6.5 Hz, CH$_3$), 2.16 (m, 2H, 2'—CH$_3$), 3.87 (s, 3H, OCH$_3$), 3.99, (s, 3H, OCH$_3$), 4.36 (bs, 2H, CH$_3$), 4.48 (overlapped m, 2H, CHNH and CHCH$_3$), 5.38 (bs, 1H, OCH), 5.71 (bs, 1H, O—

CH—O), 5.76 ( s, 1H, OCHSO$_2$), 6.96 (bd, 1H, J=7.0 Hz.NH), 7.40-7.65 (m, 3H, ArH), 8.14 (bs, 4H, ArH), 8.32 (d, 1H, J=6.88 Hz,ArH). CMR (75.44 MHz, CDCl$_3$) δ:17.0, 6'—CH$_3$; 29.0, 2'—CH$_2$; 44.8, 3'—CHNH; 50.6, CH$_2$SO$_2$; 62.1, 62.2, ArOCH$_3$; 66.6, OCHCH$_3$; 71.3, 4'—OCH; 85.7 OCHSO$_2$; 97.0, O—CH—O; 115.4, quartet, J=287.8 Hz, CF$_3$; 123.6, 130.9, p-nitrobenzoyl CH; 125.9, 127.0, 129.4, 132.5, thioxanthone, CH: 124.9, 125.5, 128.1, 128.9, 134.4, 134.7, 135.1, 148.9, 150.6, 155.4, aryl C; 157.0, quartet, J=37.7 Hz, COCF$_3$; 164.3, ester C=O; 179.8, thioxanthone C=O. The more polar epimer (38% yield) assigned as (37), had: (MP: 147°-148° C.—decomposes).

$^1$H NMR (200 MHz, CDCl$_3$) δ:1.18 (d, 3H, J=6.4 Hz, CH$_3$), 2.15 (m, 2H, 2'—CH$_2$), 3.87 (s, 3H, OCH$_3$), 3.98 (s, 3H, OCH$_3$), 4.37 (bs, 2H, CH$_2$SO$_2$), 4.69 (m, 1H, CHNH), 4.77 (bq, 1H J=6.6 Hz, CHCH$_3$), 5.38 (bs, 1H, OCH), 5.50 (bs, 1H, O—CH—O), 5.69 (s, 1H, OCHSO$_2$), 6.74 (d, 1H, J=7.3 Hz,NH), 7.40-7.64 (m, 3H, ArH), 8.17 (s, 4H, ArH), 8.33 (d, 1H, J=8.0 Hz, ArH). CMR (75.44 MHz CDCl$_3$) δ:16.8, 6'—CH$_3$; 29.5, 2'—CH$_2$; 45.6, 3'—CHNH; 51.1, CH$_2$SO$_2$; 61.9, 62.2, ArOCH$_3$; 67.2, OCHCH$_3$; 72.1, 4'—OCH; 89.0, OCHSO$_2$; 99.3, O—CH—O; 117.3, quartet, J=287.7 Hz, CF$_3$; 123.8, 131.0, p-nitrobenzoyl CH; 126.0, 127.1, 129.5, 132.6, thioxanthone CH; 124.2, 125.2, 128.2, 130.0, 132.6, 134.3, 134.7, 148.9, 150.8, 155.5 aryl C; 157.8, quartet, J=37.5 Hz, COCF$_3$: 164.8, ester C=O, 179.9 thioxanthone C=O.

EXAMPLE 3

(1S) 1-(N-trifluoroacyldaunosamine)-4,11-dimethoxy-5-oxo-5-H-1,3-dihydrothioxantheno [2,3-c] thiophene-2,2-dioxide (38)

To a solution containing 88 mg (0.12 mmol) of glycoside (36) in 5 ml of methanol was added under argon at 0° C., 0.01 ml of a 1M methanolic sodium methoxide solution. After stirring for 0.5 hr three drops of saturated aqueous ammonium chloride were added, and the reaction mixture was evaporated to dryness. The residue was dissolved in dichloromethane and the undissolved while solid was filtered off. The filtrate was evaporated to give a yellow residue to which was added 0.5 ml of CH$_2$Cl$_2$ for dissolution, followed by 30 ml of pentane. Filtration of the suspension gave a yellow precipitate found to be almost pure (38). Flash chromatography using 20% ethyl acetate in toluene gave 55 mg (78%) yield) of (1S) thioxanthyl glycoside (38). (MP: 150°-155° C. —decomposes). $^1$H NMR (300 MHz, CDCl$_3$) δ:1.40 (d, 3H, J=6.5 Hz,CH$_3$), 1.96 (dt, 1H, J=3.8,13.4 Hz,2'- HCHa), 2.14 (dd, 1H, J=5.0, 13.5 Hz,2'-HCHe), 3.66 (bs, 1H, 4'—OCH), 4.01(s, 3H, OCH$_3$), 4.07 (s, 3H, OCH$_3$), 4.37 (overlapped m, 2H, 3'—CH and 5'—OCH), 4.46 (d, 2H, CH$_2$SO$_2$), 5.71 (bd, 1H, J<3.1 Hz,O—CH—O), 5.88 (s, 1H, O—CHSO$_2$), 6.80 (bd, 1H, J=8.7 Hz,NH), 7.50-7.70 (m, 3H, ArH), 8.50 (dd, 1H, J=0.8,7.5 Hz,ArH). CMR (75.44 MHz, CDCl$_3$) δ 16.7, 6'—CH$_3$; 28.5, 2'—CH$_2$; 45.4, 3'—CH; 50.4, CH$_2$SO$_2$; 62.2, 2XArOCH$_3$; 67.3, 5'—CH; 68.7, 4'—CH; 85.3, OCHSO$_2$; 96.8, O—CH—O; 117.7 quartet, J-285.9 Hz, CF$_3$; 125.4, 129.2, 129.8, 132.7, aryl CH; 126.1, 127.2, 128.4, 129.7, 130.9, 134.9, 149.2, 155.8, aryl C; 156.5, quartet, J=37.5 Hz, COCH$_3$; 180.3, C=O.

EXAMPLE 4

(1S) 1-daunosamine-4-11-dimethoxy-5-oxo-5-H-1,3-dihydrothioxantheno [2,3-c] thiophene-2,2-dioxide (39)

A solution containing 30 mg (0.05 mmol) of glycoside (38) in 1 ml of THF was stirred for 0.5 hr at room temperature with 10 ml of a 0.1M aqueous NaOH solution. The reaction mixture was then neutralized with 1M aqueous HCl and evaporated to dryness. The residue was then stirred with 5 ml of dichloromethane, then filtered and the precipitate was triturated three times with ethylacetate. The combined organic filtrate was evaporated to dryness. Recrystallization of the residue from dichloromethane pentane gave 20.5 mg (81% yield) of thioxanthylglycoside (39) (BCH-255). (MP: 139°-141° C. decomposes). $^1$H NMR (300 MHz,CDCl$_3$) δ:1.21 (bd, 3H, J=6.4 Hz, 6'—CH$_3$), 2.12 (m, 2H, 2'—CH$_2$), 3.62 (bs, 1H, 4'—OCH), 3.83 (s, 3H, OCH$_3$), 3.93 (s, 3H, OCH$_3$), 4.11 (m, 1H, 3'—CH), 4.27 (m, 5'—OCH), 4.34 (bs, 2H, O—CH—SO$_2$), 5.58 (bs, 1H, O—CH—O), 5.77 (s, 1H, O—CH—SO$_2$), 7.35-7.55 (m, 3H, ArH), 7.90 (bs, 2H, NH$_2$), 8.33 (d, 1H, J=7.7 Hz,ArH).

EXAMPLE 5

(1R) 1-(N-trifluoroacyl)daunosamine)-4,11-dimethoxy-5-oxo-5-H-1,3-dihydrothioxantheno [2,3-c] thiophene-2,2-dioxide (40)

Following the procedure described for compound (38), 15 mg (74% yield) of (1R) thioxanthyl glycoside (40) was obtained from the catalytic methanolysis of 22 mg (0.04 mmol) of (37), (MP: 144°-148° C. —decomposes). $^1$H NMR (300 MHz, CDCl$_3$) δ:1.32 (d, 3H, J=6.6 Hz, 6'—CH$_3$), 1.96 (dt, 1H, J=3.9,13.5 Hz,2'-HCHa), 2.10 (dd, 1H, J=5.4 13.6 Hz,2'-HCHe), 3.72 (bs, 1H, 4'—OCH), 3.98 (s, 3H, OCH$_3$), 4.03 (s, 3H, OCH$_3$), 4.44 (s, 2H, CH$_2$SO$_2$), 4.47 (m, 1H, 3'—CH), 4.66 (bq, 1H, J=6.6 Hz,5'—CH), 5.44 (bd, 1H, J<3.5 Hz,O—CH—O), 5.73 (s, 3H, OCHSO$_2$), 6.79 (bd, 1H, J=8.5 Hz.NH), 7.5-7.55 (m, 3H, ArH), 8.48 (dd, 1H, J=1.3, 8.0 Hz,ArH).

The (1R) isomer of the compound (39), i.e. compound (41), may be synthesized by treating the (1R) compound (40) with sodium hydroxide according to the above technique.

EXAMPLE 6

Antitumor Activity

BCH-255 (compound 39) was subjected to an in vitro cytotoxicity evaluation against 59 tumor cell lines to assess its potential as an anticancer drug. These assays were carried out at the Developmental Therapeutics Program, Division of Cancer Treatment, National Cancer Institute (Bethesda, Md., USA). The method consists of incubating varying concentrations of the drug with an inoculum of cells for two days. At the end of the assay, the number of viable cells is estimated with a dye, sulforhodamine B. The protocol is described in M. R. Boyd, "Status of the NCI Preclinical Antitumor Drug Discovery Screen", Principles and Practices of Oncology, 3, pp. 1-12, 1989.

There are three parameters calculated: GI$_{50}$, the log molar concentration of drug required to inhibit cell growth by 50%; TGI, the log molar concentration of drug required to completely block cell growth; $LC_{50}$, the log molar concentration of drug required to reduce the original cell number by 50%. It should be noted that the first two parameters ($GI_{50}$ and TGI) relate to antiproliferation effects while the third one ($LC_{50}$) indicates true cytotoxicity. The results are presented in the Table below.

ANTIPROLIFERATIVE AND CYTOTOXIC EFFECTS OF BCH-255 IN TUMOR CELL LINES

| Panel/Cell Line | $LOG_{10}GI50$ | $Log_{10}TGI$ | $Log_{10}LC50$ |
|---|---|---|---|
| Leukemia | | | |
| CCRF-CEM | −4.75 | −4.38 | −4.01 |
| HI-60TB | −4.80 | −4.48 | −4.16 |
| K-562 | −4.79 | −4.44 | −4.08 |
| MOLT-4 | −4.72 | −4.39 | −4.06 |
| RPMI-8226 | −4.79 | −4.39 | >−4.00 |
| SR-WJU | | | |
| Non-Small Cell Lung Cancer | | | |
| A-549/ATCC | −4.71 | −4.44 | −4.16 |
| FKVX | −4.59 | −4.31 | −4.03 |
| HOP-18 | >−4.00 | >−4.00 | >−4.00 |
| HOP-62 | | | |
| HOP-92 | | | |
| NCI-H226 | −4.70 | −4.39 | −4.08 |
| NCI-H23 | −4.30 | >−4.00 | >−4.00 |
| NCI=H322M | −4.72 | −4.36 | −4.00 |
| NCI-H460 | −4.69 | −4.40 | −4.10 |
| NCI-H522 | −4.73 | −4.42 | −4.11 |
| LXFL-529L | −4.77 | −4.50 | −4.24 |
| Small Cell Lung Cancer | | | |
| DMS 114 | −4.75 | −4.43 | 4.11 |
| DMS 273 | −4.74 | −4.45 | −4.15 |
| Colon Cancer | | | |
| Colo 205 | −4.75 | −4.43 | −4.11 |
| DLD-1 | −4.61 | −4.17 | >−4.00 |
| HCC-2998 | | | |
| HCT-116 | −4.69 | −4.40 | −4.12 |
| HCT-15 | −4.72 | −4.37 | −4.02 |
| HT 29 | −4.75 | −4.48 | −4.21 |
| KM 12 | −4.74 | −4.40 | −4.06 |
| MK20L2 | −4.77 | −4.51 | −4.24 |
| SW-620 | −4.69 | −4.43 | −4.17 |
| CNS Cancer | | | |
| SF-268 | −4.68 | −4.28 | >−4.00 |
| SF-295 | −4.79 | −4.49 | −4.20 |
| SF-539 | −4.76 | −4.50 | −4.24 |
| SNB-19 | −4.51 | >−4.00 | >−4.00 |
| SNB-75 | −4.80 | −4.52 | −4.24 |
| SNB-78 | −4.69 | −4.37 | −4.04 |
| U251 | −4.76 | −4.50 | −4.25 |
| F498 | −4.78 | −4.50 | −4.23 |
| Melanoma | | | |
| LOX IMVI | −4.75 | −4.42 | −4.09 |
| MALME-3M | −4.70 | −4.44 | −4.17 |
| M14 | −4.74 | −4.48 | −4.22 |
| M19-MEL | −4.74 | −4.46 | −4.17 |
| SK-MEL-2 | 4.72 | −4.44 | −4.15 |
| SK-MEL-28 | 4.74 | −4.46 | −4.17 |
| SK-MEL-5 | −4.74 | −4.49 | −4.24 |
| UACC-257 | −4.65 | −4.36 | −4.07 |
| UACC-62 | −4.72 | −4.43 | −4.13 |
| Ovarian Cancer | | | |
| IGROV-1 | −4.78 | −4.42 | −4.06 |
| OVCAR-3 | −4.81 | −4.50 | −4.19 |
| OVCAR-4 | −4.74 | −4.46 | −4.19 |
| OVCAR-5 | −4.40 | >−4.00 | >−4.00 |
| OVCAR-8 | −4.71 | −4.42 | −4.13 |
| SK-OV-3 | −4.72 | −4.39 | −4.07 |
| Renal Cancer | | | |
| 786-O | −4.79 | −4.51 | −4.23 |
| ACHN | −4.76 | −4.49 | −4.21 |
| CAKI-1 | −4.71 | −4.42 | −4.13 |
| RXF-393 | −4.77 | −4.45 | −4.14 |
| RXF-631 | −4.70 | −4.33 | >−4.00 |
| SN12C | −4.74 | −4.44 | −4.14 |
| TK-10 | −4.59 | −4.35 | −4.11 |
| UO-31 | −4.71 | −4.37 | −4.04 |
| MG MID | −4.70 | −4.39 | −4.12 |
| DELTA | 0.11 | 0.13 | 0.13 |
| RANGE | 0.81 | 0.52 | 0.25 |

As evidenced in the Table, all the cell lines of solid tumors and leukemia showed cytotxcity to the drug. It is interesting to note that such a structure as BCH-255 possesses a wide spectrum of antitumor activity. BCH-255 in effect represents an example from a totally novel class of antitumor drugs.

It is claimed:

1. A compound of the formula

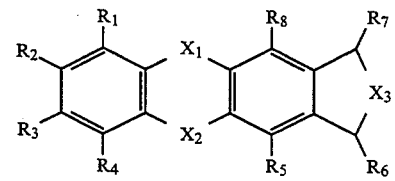

$X_1$ is C=O;

$X_2$ is S;

$X_3$ is selected from the group consisting of
S and
$SO_2$ $R_1$, $R_2$, $R_3$, $R_4$, $R_5$ and $R_8$ are independently selected from group consisting of
hydrogen,
$C_{1-16}$ alkyl, and
$C_{1-16}$ alkoxy, $R_7$ is hydrogen;

$R_6$ is a monosaccharide of the formula

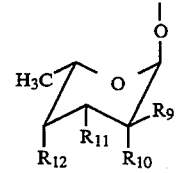

wherein $R_9$ and $R_{10}$ are each hydrogen $R_{11}$ is selected from the group consisting of
amino, and
trifluoro $C_{1-16}$ acylated amino; and $R_{12}$ is selected from the group consisting of
hydrogen,
hydroxyl or its tetrahydropranyl ether,
halogen, and
benzoate which may be unsubstituted or substituted by nitro,
inclusive of the 1S and 1R isomers and the pharmaceutically acceptable salts thereof.

2. A compound according to claim 1, wherein
$R_1$, $R_2$, $R_3$, $R_4$, $R_5$ and $R_8$ are independently selected from the group consisting of
hydrogen, and
$C_{1-4}$ alkoxy, $R_6$ is a monosaccharide of the formula

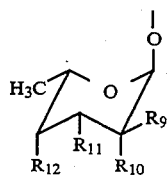

wherein

R$_9$ and R$_{10}$ are as defined in claim 1;
R$_{11}$ is selected from the group consisting of amino, and
trifluoro C$_{1-8}$ acylated amino, and
R$_{12}$ is as defined in claim 1.

3. A compound according to claim 1, wherein
R$_1$, R$_2$, R$_3$, R$_4$, R$_5$ and R$_8$ are independently selected from the group consisting of hydrogen methoxy.

4. A compound according to claim 1, wherein
R$_1$, R$_2$, R$_3$, R$_4$, R$_5$ and R$_8$ are each hydrogen.

5. The compound of claim 1 which is (1R) 1-(4'-O-p-nitrobenzoyl-N-trifluoroacyldaunosamine)-4,11-dimethoxy-5-oxo-5-H-1,3-dihydrothioxantheno [2,3-c] thiophene-2,2-dioxide (37).

6. The compound of claim 1 which is (1S) 1-(4'-O-p-nitrobenzoyl-N-trifluoroacyldaunosamine)-4,11-dimethoxy-5-oxo-5-H-1,3-dihydrothioxantheno [2,3-c] thiophene-2,2-dioxide (36).

7. The compound of claim 1 which is (1R) 1-(N-trifluoroacyldaunosamine)-4,11-dimethoxy-5-oxo-5-H-1,3-dihydrothioxantheno [2.3-c] thiophene-2,2-dioxide (40).

8. The compound of claim 1 which is (1S) 1-(N-trifluoroacyldaunosamine)-4,11-dimethoxy-5-oxo-5-H-1,3-dihydrothioxantheno [2,3-c] thiophene-2,2-dioxide (38).

9. The compound of claim 1 which is (1R) 1-daunosamine-4-11-dimethoxy-5-oxo-5-H-1,3-dihydrothioxantheno [2,3-c] thiophene-2,2-dioxide (41).

10. The compound of claim 1 which is (1S) 1-daunosamine-4-11-dimethoxy-5-oxo-5-H-1,3-dihydrothioxantheno [2,3-c] thiophene-2,2-dioxide (39).

11. A compound of the formula

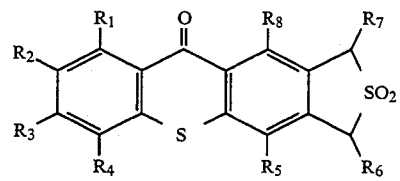

wherein R$_1$, R$_2$, R$_3$, R$_4$, R$_5$, R$_6$, R$_7$ and R$_8$ are as defined in claim 1.

12. A pharmaceutical composition, comprising an effective amount of at least one compound according to claim 1 and a pharmaceutically acceptable carrier.

13. A pharmaceutical composition, comprising an effective amount of at least one compound according to claim 2 and a pharmaceutically acceptable carrier.

14. A pharmaceutical composition, comprising an effective amount of at least one compound according to claim 3 and a pharmaceutically acceptable carrier.

15. A pharmaceutical composition, comprising an effective amount of at least one compound according to claim 4 and a pharmaceutically acceptable carrier.

16. A pharmaceutical composition, comprising an effective amount of a compound according to claim 5, and a pharmaceutically acceptable carrier.

17. A pharmaceutical composition, comprising an effective amount of a compound according to claim 6, and a pharmaceutically acceptable carrier.

18. A pharmaceutical composition, comprising an effective amount of a compound according to claim 7, and a pharmaceutically acceptable carrier.

19. A pharmaceutical composition, comprising an effective amount of at least one compound according to claim 8, and a pharmaceutically acceptable carrier.

20. A pharmaceutical composition, comprising an effective amount of at least one compound according to claim 9, and a pharmaceutically acceptable carrier.

21. A pharmaceutical composition, comprising an effective amount of at least one compound according to claim 10, and a pharmaceutically acceptable carrier.

22. A pharmaceutical composition, comprising an effective amount at least one compound as claimed in claim 11, and a pharmaceutically acceptable carrier.

* * * * *